United States Patent
Zourob

(10) Patent No.: US 10,337,047 B2
(45) Date of Patent: Jul. 2, 2019

(54) ASSAY FOR EARLY DETECTION OF A DISEASE USING A MAGNETIC NANOPARTICLE BIOSENSOR

(71) Applicant: Mohammed Zourob, Riyadh (SA)

(72) Inventor: Mohammed Zourob, Riyadh (SA)

(73) Assignee: Alfaisal University, Riyadh (SA)

( * ) Notice: Subject to any disclaimer, the term of this patent is extended or adjusted under 35 U.S.C. 154(b) by 591 days.

(21) Appl. No.: 14/819,195

(22) Filed: Aug. 5, 2015

(65) Prior Publication Data
US 2017/0037450 A1    Feb. 9, 2017

(51) Int. Cl.
*C12Q 1/37* (2006.01)

(52) U.S. Cl.
CPC ...... *C12Q 1/37* (2013.01); *G01N 2333/96433* (2013.01); *G01N 2446/20* (2013.01); *G01N 2446/80* (2013.01); *G01N 2800/18* (2013.01); *G01N 2800/26* (2013.01)

(58) Field of Classification Search
CPC ............ C12Q 1/6834; C12Q 2563/143; G01N 33/54326; G01N 33/558; G01N 33/54366; G01N 33/56911; G01N 21/78; G01N 33/5434; G01N 33/553; G01N 33/54346; G01N 33/54353; B01L 2400/0406; B01L 2300/0825; B01L 2400/043; B01L 3/502715
See application file for complete search history.

(56) References Cited

U.S. PATENT DOCUMENTS

| | | | |
|---|---|---|---|
| 2005/0100930 A1* | 5/2005 | Wang | B82Y 5/00 435/6.12 |
| 2010/0297683 A1* | 11/2010 | Krause | C12Q 1/001 435/23 |

OTHER PUBLICATIONS

Esseghaier et al. (Biosensors and Bioelectronics 41 (2013) 335-341) (Year: 2013).*
Zheng et al. (Faraday Discussions, 2011, 149, 37-47) (Year: 2011).*

* cited by examiner

*Primary Examiner* — Sally A Merkling
(74) *Attorney, Agent, or Firm* — Geeta Kadambi; Riddhi IP LLC

(57) ABSTRACT

A multiplex hand-held diagnostic biosensor, using two inflammatory salivary biomarkers, Human Neutrophil Elastase (HNE) and Cathepsin-G, was constructed made to potentially detect Periodontitis at an early stage is described. The use of magnetic nanoparticle biosensor method used as a device was based on the measurement of proteolytic activity using specific proteases probes. The magnetic nanoparticle biosensor device is capable of specific and quantitative detection of HNE and Cathepsin-G in solution and in spiked saliva samples with a lower detection limit of 1 pg/mL and 100 fg/mL for HNE and Cathepsin-G, respectively.

5 Claims, 15 Drawing Sheets

Specification includes a Sequence Listing.

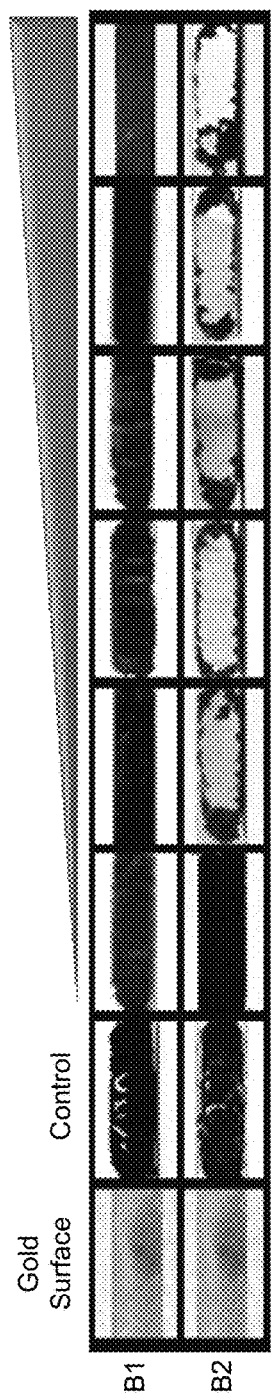
FIG. 2A
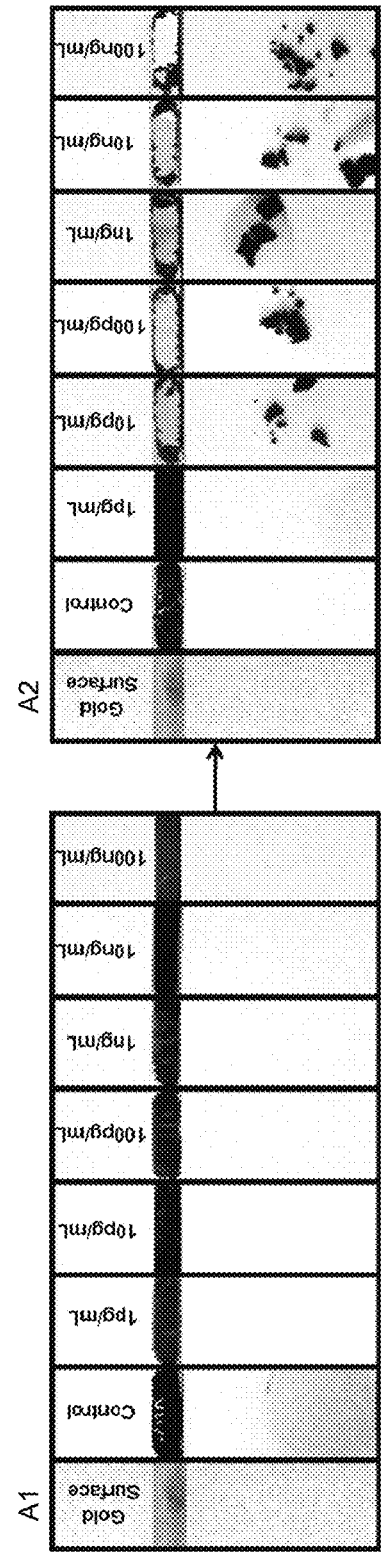
FIG. 2B
FIG. 2C

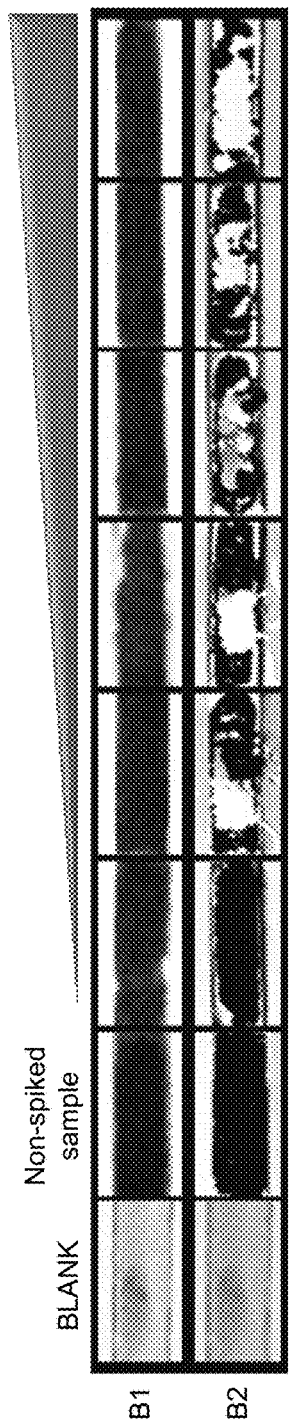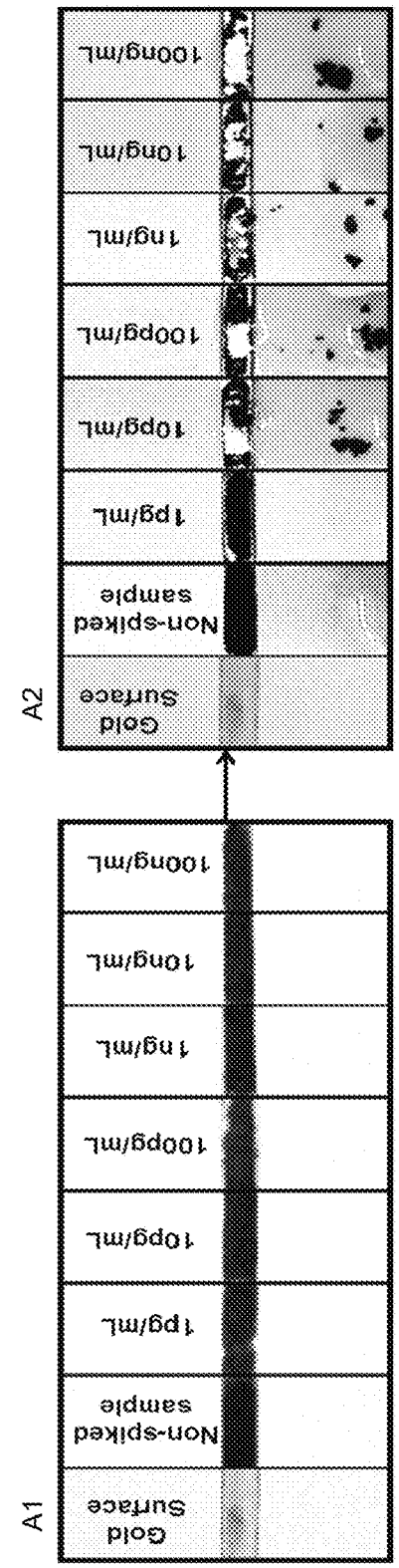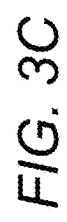
FIG. 3A
FIG. 3B
FIG. 3C

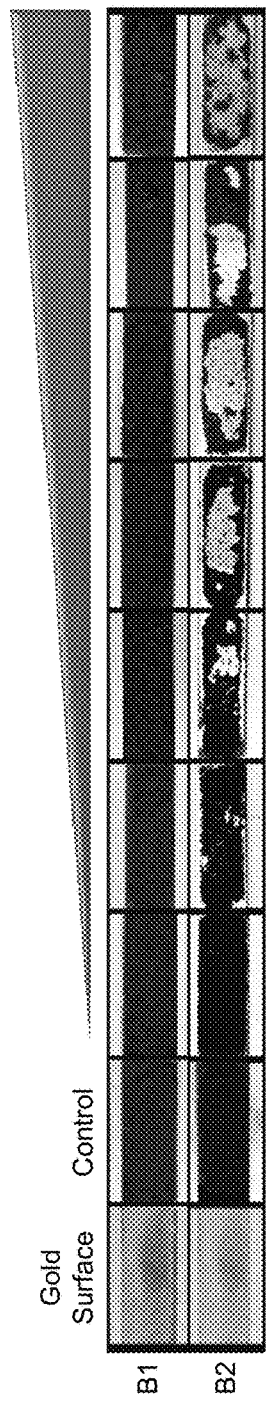
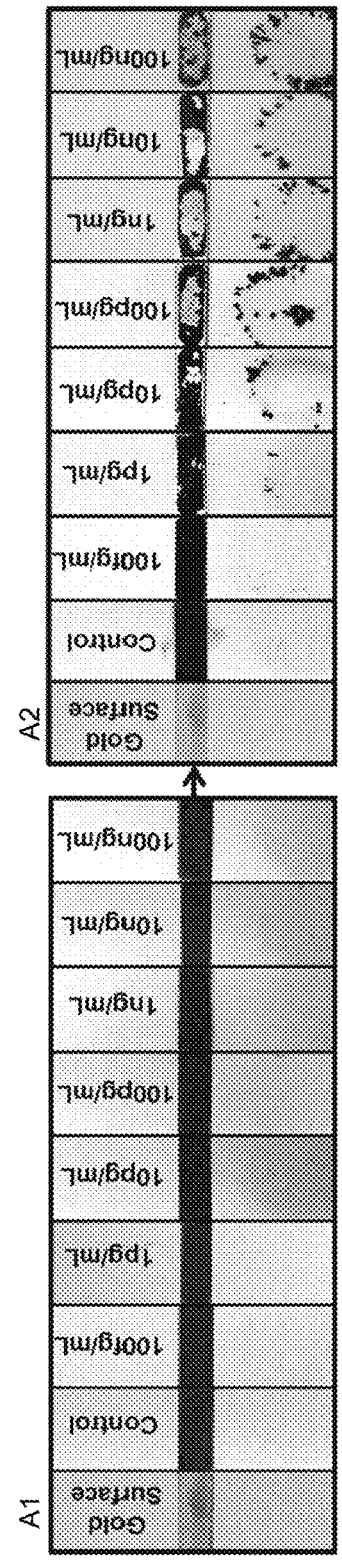
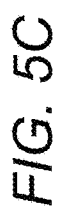
FIG. 5A
FIG. 5B
FIG. 5C

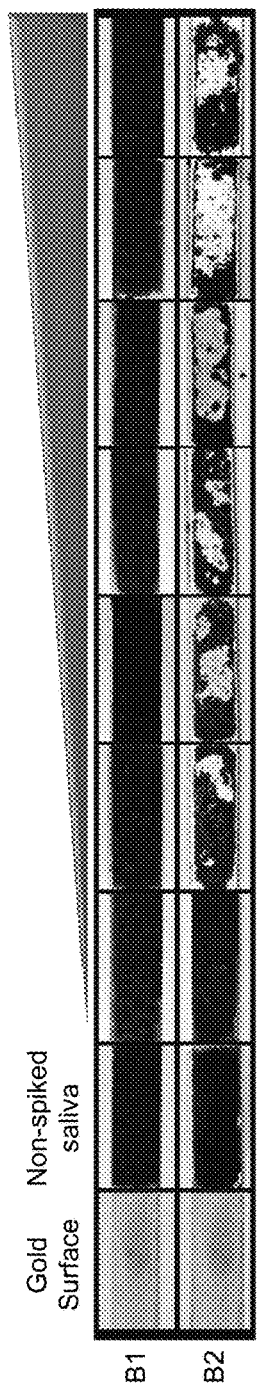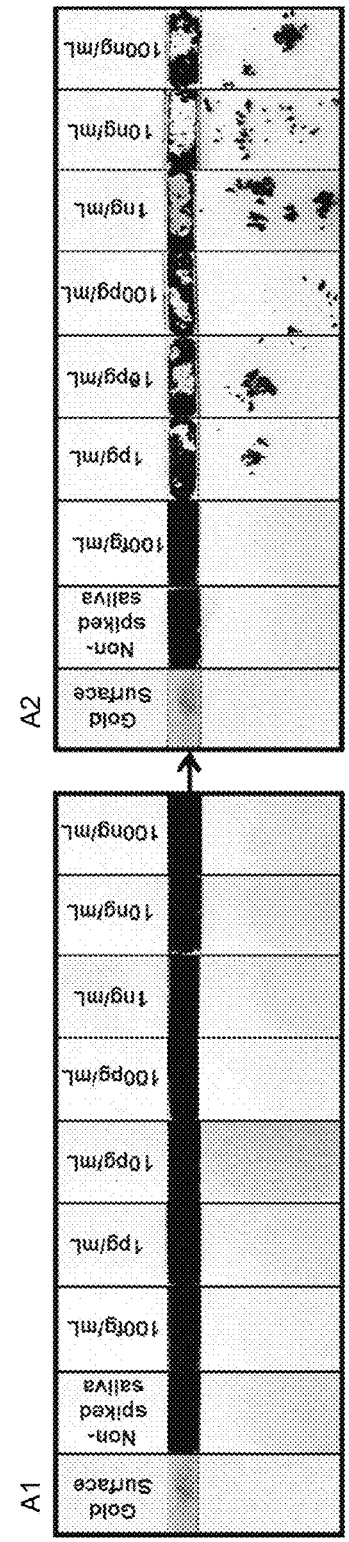
FIG. 6A
FIG. 6B
FIG. 6C

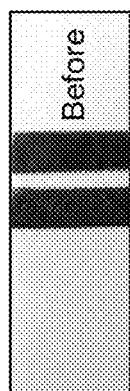
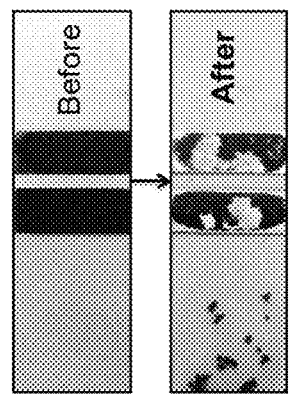
Cathepsin-G: 0
HNE: 100
*FIG. 10A*
Cathepsin-G: 25
HNE: 75
*FIG. 10B*
Cathepsin-G: 50
HNE: 50
*FIG. 10C*
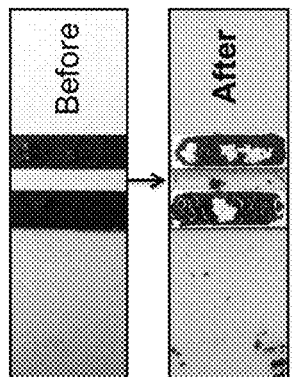
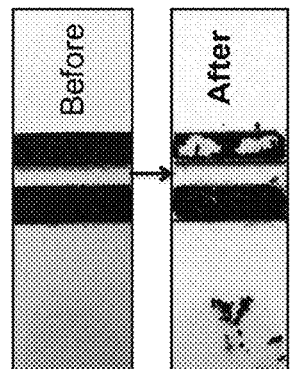
Cathepsin-G: 75
HNE: 25
*FIG. 10D*
Cathepsin-G: 100
HNE: 0
*FIG. 10E*

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: Peptide

<400> SEQUENCE: 1

Gly Ser Gly Ser Gly Gly Gly Ala Ala Pro Val Ala Ala Lys Gly Gly
1               5                   10                  15

Gly Ser Gly Ser Cys
            20

<210> SEQ ID NO 2
<211> LENGTH: 9
<212> TYPE: PRT
<213> ORGANISM: Artificial Sequence
<220> FEATURE:
<223> OTHER INFORMATION: Peptide

<400> SEQUENCE: 2

Gly Pro Gln Gly Ile Trp Gly Gln Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Peptide

<400> SEQUENCE: 3

Ala Ala Pro Pro Phe Phe Lys
1               5

<210> SEQ ID NO 4
<211> LENGTH: 7
<212> TYPE: PRT
<213> ORGANISM: Artificial Sequence
```

-continued

```
<220> FEATURE:
<223> OTHER INFORMATION: Peptide

<400> SEQUENCE: 4

Ala Ala Pro Val Ala Ala Lys
1               5
```

ASSAY FOR EARLY DETECTION OF A DISEASE USING A MAGNETIC NANOPARTICLE BIOSENSOR

CROSS REFERENCE TO SEQUENCE FILE

This application contains sequence listing that has been submitted as an ASCII file named RIPLLC032.004US1_ST25, the date of creation Oct. 10, 2018, and the size of the ASCII text file in bytes is 2 kb.

FIELD OF TECHNOLOGY

The present disclosure relates to a novel assay for detection of a disease state using a magnetic nanoparticle biosensor. More specifically an assay of biomarkers for a specific disease using a magnetic nanoparticle biosensor to identify the presence and intensity, progression of disease, efficacy of treatment or absence of disease in mammal is described.

BACKGROUND

Many diseases have early and chronic stage manifestation of biomarkers that help identify the disease. Most diseases are well characterized and if detected early no irreparable harm can be inflicted on a person. For example, Periodontitis is a chronic disease which affects at least 10% of the population. If untreated, Periodontitis can lead to teeth loss. Unfortunately, current diagnostic tests are limited in their sensitivity and specificity. It is characterized by apical migration of epithelial attachment, loss of connective tissue, alveolar bone and eventually tooth. Periodontitis progression is usually site specific, but is not consistent. Thus, it is difficult to clinically distinguish the progressing from the non-progressing inflamed sites. Moreover, the early stages of periodontal disease progression, particularly gingivitis, are often difficult to quantify because of the lack of a linear measurement tool.

In clinical practice, Periodontitis can be diagnosed by radiographic examinations. But still the best available diagnostic aid is the measurement of the depth of the tooth pocket. However, this only provides a retrospective analysis mostly when tooth attachment has already been lost. So, the current diagnostic methodologies are limited to identify the cause of disease or patients at risk. In addition the clinical practice conducted by dentists, different microbiological and biochemical methods such as culturing, DNA probing and polymerase chain reaction (PCR) are employed to detect bacteria in samples from periodontal pockets. A general drawback of methods is that they do not quantify the severity of the disease.

So far, several studies aimed to develop new rapid point-of-care devices for the detection of Periodontal diseases, using markers that pinpoint the severity of Periodontitis. For example, Ivnitski et al, (2003) have used a hand-held non-invasive electrochemical amperometric device to detect salivary peroxidase, which is related to periodontitis. However, this method is nonspecific, expensive and time consuming.

Another example is the benzoyl-DL-arginine-naphthylamide (BANA) test strips that were developed by Loesche et al, (1990, 1992) and are currently in the market. This strip detects various bacteria (*Treponema denticola, Porphyromonas gingivalis* and *Bacteroides forsythus*) found in adult periodontal plaque. Even though, this method has been in the market for a while, but the strip only detects periopathogens and lack sensitivity and specificity.

There were a few other studies conducted to detect periodontitis using bacterial protease activity such as *P. gingivalis* as a marker. For instance earlier highly bacteria-specific fluorescence resonance energy transfer (FRET) peptides were generated to detect the proteolytic activity of *P. gingivalis* in vitro and in situ. The value of these substrates are beyond doubt, though, as protease activity in cases of periodontitis is a mixture of both host and microbiological origin these substrates only cover one part of the palet.

In the human oral cavity, there are around 700 microbial species. Previous studies have implicated Gram-negative anaerobic bacteria (called perio-pathogens) as the causative agents of periodontal diseases. A specific bacterial group, the "red complex" group which includes *Porphyromonas gingivalis, Tannerella forsythia* and *Treponema denticola*, have been strongly associated with the clinical signs of advanced periodontal lesions. The current understanding of the pathogenesis of periodontitis suggests that the modulation of host response by bacterial products such as lipopolysaccharide and proteases are important factors in disease onset and progression.

As an effective host feedback response to bacterial challenge, neutrophils influx increases into gingival crevice. Neutrophils play a destructive role in the process of periodontal tissue breakdown due to the production of high levels of Human Neutrophil Elastase (HNE). This enzyme is a serine protease, which degrades elastin and other functionally and structurally important proteins in the periodontium during the inflammatory process. During which increased levels are found in the gingival crevicular fluid (GCF). In GCF the metabolic products of neutrophils, like HNE, are elevated and associated with periodontal inflammation. These proteins can thus be used as potential indicator for inflammation severity at individual sites. Notably, it is not only the amounts of this protease that differ, but also, the activity of the protease. For example, more elastase remains active in GCF during periodontal disease.

Another host-cell derived serine protease with potential for Periodontitis diagnosis is Cathepsin-G. In response to periodontitis this protease is secreted in the extracellular spaces where they degrade gingival tissue components such as collagen. Furthermore, there is an indication that Cathepsin-G is linked with the progression of gingivitis and chronic adult periodontitis. Immuno-histochemical studies of Cathepsin-G have shown that the protease is expressed and localized in the inflamed gingiva in an increased activity along with the severity of periodontal inflammation. These results suggested the possible involvement of Cathepsin-G in the degradation of inflamed gingival connective tissue since it was reported that Cathepsin-G level was elevated in the GCF.

To date, several methods have been described for elastase detection. These include chromatography, sephadex-gel-electrophoresis, and radioimmunoassay. Similarly, there are several studies which focus on the degradation of hydrogel films cross-linked with peptides such as HNE, Cathepsin-G and matrix metalloproteinase-8 (MMP-8), monitored using a combination of quartz crystal microbalance (QCM) and electrochemical impedance measurements. However even though these methods were recently introduced, there is some drawback by being complex and time consuming. There is need for a rapid point-of-care diagnostic detection

SUMMARY

In the instant disclosure we present a novel assay for detection of a disease state using a magnetic nanoparticle biosensor device. In one embodiment, a one step or a multiplex rapid point-of-care diagnostic system, which is noninvasive using a magnetic nanoparticle biosensor in a mammal fluid sample with the help of biomarkers are described.

In one embodiment, magnetic nanoparticle biosensor device (device), also mentioned as sensing support, comprising of a magnetic nanoparticle (magnetic carrier), a substrate hosted by the magnetic nanoparticle, a magnet, a sensor support and a marker is developed. The device is insertable into a support tool that enables the user to collect the sample. The device may also be embedded into a support and can be disposed after one use.

In another embodiment, a support tool containing the device may be used for collecting the sample in vivo, on spot collection of sample and as a point of care diagnostic kit etc. A support tool in another embodiment comprises of a dentist tools, syringe, swab, a dropper, paper sensor support, dentists tools, cotton, polymers, piece of cotton, piece of cloths, or any other metal sensor support which is dielectric or an insulator, any other small instrument that may come in contact with a biological fluid and enable it to flow or collect and deliver it to a magnetic nanoparticle biosensor device.

In one embodiment, the sensor support is at least one of a gold, carbon, silica and glass. In one embodiment, the magnetic beads may be of micro size or nano size magnetic beads or any colored beads that can attach to the sensor support.

In another embodiment, the marker may be associated with diseases such as peridotites, hepatitis, lunch infections, tetanus, or any other proteolytic enzyme, combination thereof and nor not limited to just these.

In one embodiment, the substrate hosted by the magnetic nanoparticle comprises of a spacer, wherein the spacer is at least one of a peptide, a polymeric linker or any other suitable linker. A method of reacting, detecting, and measuring the presence and intensity and absence of a disease is done using the magnetic nanoparticle biosensor beads is described. The magnetic nanoparticle biosensor beads supported by a sensor support may be embedded, carried or attached to any tool that a professional might use for collecting biological samples.

In one embodiment, collecting a biological sample using a support tool embedded with a magnetic nanoparticle biosensor; attaching a marker peptide coupled carboxy terminated magnetic bead to a gold sensor support using a specific method; reacting the biological sample and the marker peptide coupled carboxy terminated magnetic bead to form a conjugate; and measuring to detect an association or dissociation of the conjugate on the gold sensor support for presence and intensity or absence of the disease in a mammal.

A method to detect a disease having a marker enzyme comprises of providing a sample from a patient; providing a sensing support comprising a plurality of substrates each having a cleavage site cleavable by an enzyme associated to the disease, a sensor support and a magnetic carrier, the substrate having at one end thereof first attachment means for attachment to the magnetic carrier and at another end thereof second attachment means for attachment to the sensor support; wherein upon addition of the sample to the attached substrate, the substrate is cleaved and a section of the substrate comprising the magnetic carrier is drawn to the magnetic means while the other section of the substrate remains attached to the sensor support, which is measured using a specific mean, which is indicative of the presence of the disease in the patient.

In one embodiment the specific mean would be using at least one of an electrochemical impedance (cyclic voltammetry) technique, electrochemical technique, optical (surface plasmon resonance (SPR) or localized surface plasmon resonance (LSPR)), optical waveguide, mass sensitive sensors, surface enhanced Raman spectroscopy (SERS), colorimetric technique and a combination thereof.

Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which:

FIG. 2A shows zoomed in visual comparison of the golden color of the exposed probe before (B1) and after (B2) HNE activity. FIGS. 2B and 2C shows assay results of HNE sensor probe (specific HNE substrate peptide covalently bound to a magnetic bead) under the effect of different HNE concentrations image of the biosensor before pipetting different concentrations of HNE enzyme, image of the assay after pipetting different concentrations of HNE enzyme on a gold sensor support device.

FIG. 3A shows zoomed in visual comparison of the golden color of the saliva testing and FIGS. 3B and 3C HNE marker (specific HNE substrate peptide covalently bound to a magnetic nanoparticle bead) under the effect of different concentrations of spiked saliva image of the assay before pipetting different concentrations of spiked saliva with HNE enzyme.

FIG. 5A shows a zoomed visual comparison of the golden color exposed marker before and after Cathepsin-G activity. FIG. 5B shows blank Cathepsin-G peptides bonded to the gold sensor support and FIG. 5C shows different levels of Cathepsin-G activity and results.

FIG. 6A shows zoomed in visual comparison of the golden color of the saliva testing and FIGS. 6B and 6C Cathepsin-G sensor probe under the effect of different concentrations of spiked saliva image of the assay before pipetting different concentrations of spiked saliva with Cathepsin-G enzyme.

FIGS. 10A, 10B, 10C, 10D and 10E shows different ratio of interaction between different peptide markers.

Figure 1:
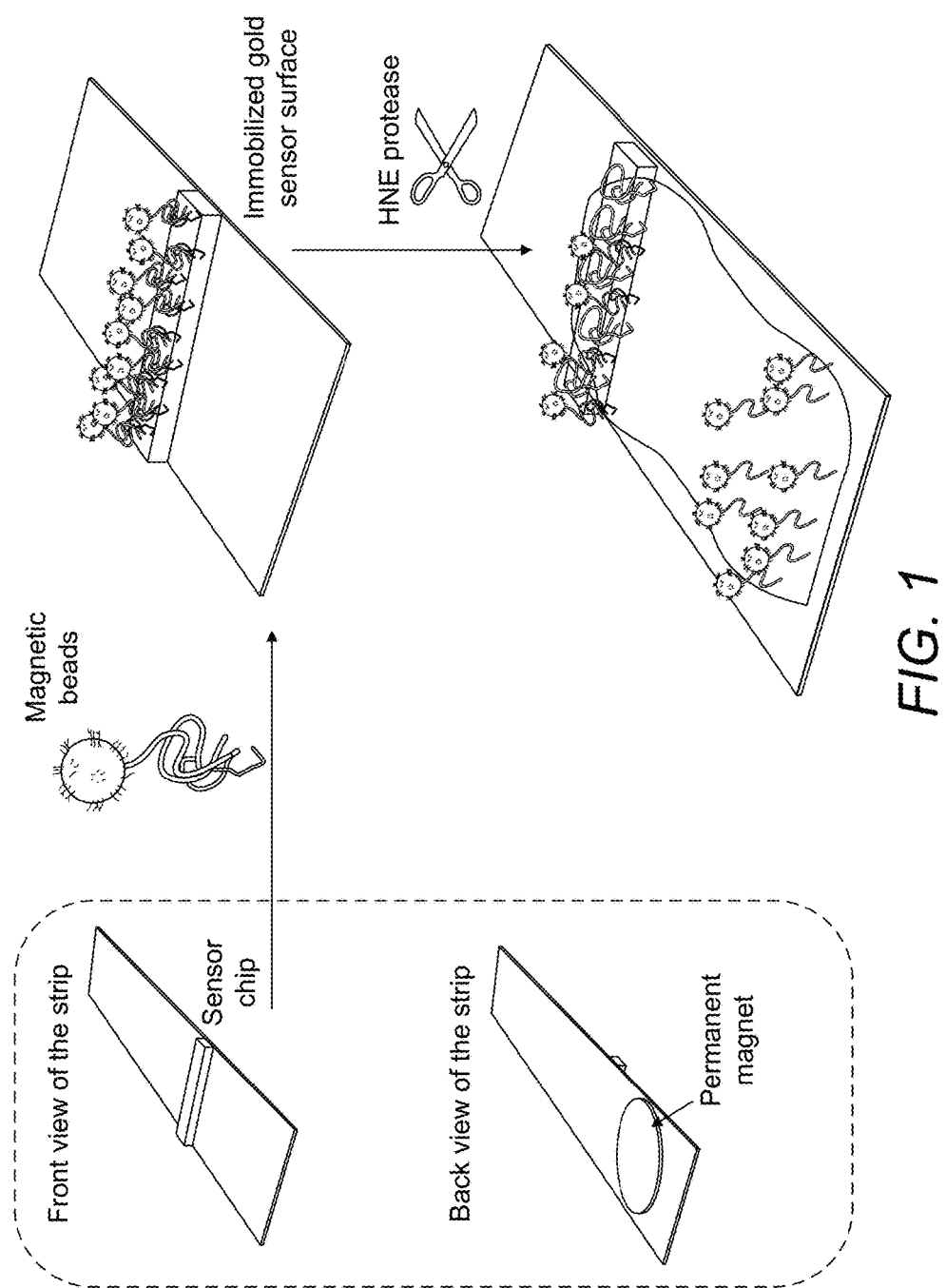
FIG. 1 shows a schematic image of the assays for detecting the HNE and Cathepsin-G's presence or absence on a gold sensor support device.

Other features of the present embodiments will be apparent from the accompanying drawings and from the detailed description that follows.

DETAILED DESCRIPTION

In the present disclosure a device and method of using the device to detect a disease, show progress of a disease, efficacy of the treatment rendered and diagnosis using a magnetic nanoparticle biosensor is described. A method to detect a disease having a marker enzyme comprises of providing a sample from a patient having a specific disease, building and providing a device for sensing comprising a plurality of substrates each having a cleavage site cleavable by an enzyme associated to the disease, a sensor support and a magnetic carrier, the substrate having at one end thereof first attachment means for attachment to the magnetic carrier and at another end thereof second attachment means for attachment to the sensor support; wherein upon addition of the sample to the attached substrate, the substrate is cleaved and a section of the substrate comprising the magnetic carrier is drawn to the magnetic means while the other section of the substrate remains attached to the sensor support, which is measured using a specific mean, which is indicative of the presence of the disease in the patient.

This developed magnetic nanoparticle biosensor is capable of monitoring HNE and Cathepsin-G protease activity separately and in unison, qualitatively and quantitatively via the degradation of the peptide substrates. To carry out periodontal diseases diagnostics, the small sensor strip is proficient for the quantitative HNE detection in solution and saliva, attaining a lower detection limit of 1 pg/mL with good specificity and reproducibility. Similarly, the small sensor strip is efficient for quantitative Cathepsin-G detection in solution and saliva, attaining a lower detection limit of 100 fg/mL with good sensitivity and reproducibility, Furthermore, this small sensor strip has been shown to be proficient as a multiplex detecting both HNE and Cathepsin-G simultaneously. Also the peptide sequences selected proved to be specific and sensitive since the enzymes reacted with the correct peptide. In addition, in a small pilot study this small sensor strip has been shown to be proficient when testing periodontal patient's samples proving that there is a potential future in using this application for the detection of periodontal diseases.

Materials and Reagents:

Carboxyl-terminated beads of 50 nm diameter were provided by Turbo beads (Switzerland) via Sigma Aldrich (Dorset, UK). Self-adhesive Magnet sheets were purchased from Polarity Magnets Company. The recombinant Human Neutrophil Elastase (HNE) was purchased from Merck Chemical (Nottingham, United Kingdom). The recombinant Cathepsin-G enzyme was purchased from Elastin Products Company Inc. The peptide sequences (HNE specific peptide: GSGSGGGAAPVAAKGGGSGSC and Cathepsin-G specific peptide: Ahx-GPQGIWGQR-Ahx) was synthesised by Pepmic Co., Ltd (Suzhou, China). The coupling agents N-Hydroxysuccinimide (NHS) and 1-(3-Dimethylaminopropyl)-3-Ethyl-Carbodiimide (EDC) and the plastic pH indicator strip were purchased from Sigma Aldrich (Dorset, UK). The self-adhesive tape was purchased from Whatman (London, U.K). The wash/storage buffer (10 mM Tris base, 0.15 M Sodium Chloride, 0.1% (w/v) Bovine Serum Albumin, 1 mM Ethylenediaminetetraacetic acid (EDTA), 0.1% Sodium Azide, pH 7.5), the coupling buffer (10 mM Potassium Phosphate, 0.15 M Sodium Chloride, pH 5.5), the HNE reaction buffer (100 mM Tris-HCl, 500 mM sodium Chloride, pH7.5) and Cathepsin-G assay buffer (0.05M Sodium Acetate, 0.1M Sodium Chloride, pH5) were prepared from chemicals of analytical grade.

Conjugation of the Human Neutrophil Elastase (HNE) and Cathepsin-G Substrate Peptides to Magnetic Beads to Make Magnetic Nanoparticle Biosensor The magnetic bead suspension (150 mg/mL) was placed in an ultrasonic bath (Grant, XUBA3 model, Spain) for 5 minutes at full frequency of 44 KHz and three times washed with coupling buffer. After washing, the beads were mixed with the peptide (1.0 mg/mL) and the coupling agents EDC (0.57 mg/mL) and NHS (12 µg/mL). The mixture was shaken gently at room temperature for 24 hours. Any uncoupled peptides were removed by washing the beads 3 times with washing buffer. Finally, the beads were stored at 4° C. in storage/wash buffer until use. These beads are carboxy terminated magnetic beads.

Gold Sensor Support Preparation

Clear adhesive tape was plated with a thin layer (30 nm) of gold. Subsequently, a narrow piece (1.5-2.0 mm in width) was cut and stacked over the plastic pH strip to provide a physical support for the bio-functionalization process of the detective sensor.

Sensing Monolayer Immobilization

The HNE and Cathepsin-G magnetic-peptide solution (marker peptide) was mounted over the gold sensing surface and left at room temperature until dry. Consequently, an external magnetic field was applied using a permanent magnet with field strength of 3360 gauss and 573 gauss at 1 mm and 10 mm distance, respectively. The magnet was passed over the functionalized strip from a distance of 3 to 5 mm to remove any non-immobilized magnetic beads. This is the specific method by which a gold sensor support is made and embedded or inserted in various diagnostic and measuring devices.

Biosensing of HNE

The current detection method is based on the measurement of HNE proteolytic activity using a specific substrate peptide. The probe was designed to be specific for HNE. Accordingly, the substrate sequence AAPVAAK, with an 8-residue linker on either terminal of the peptide was used. The N-terminal of the peptide was attached to the magnetic bead. A cysteine residue was inserted at the C-terminal, permitting a gold-sulphur irreversible interaction for the establishment of a self-assembled monolayer (SAM) of peptide and magnetic bead on the surface of the sensor support (FIG. 1). Conversely, a round permanent paper magnet was fitted on the back and beneath the support. Next, the HNE enzyme was dropped over the functionalized sensor support. During the proteolytic cleavage, the permanent magnet would attract the cleaved magnetic beads and cause a visual observation of the bright gold surface, affording qualitative evaluation of the examined samples. In addition, a quantitative evaluation was manageable by using different concentrations of HNE solution (100 ng/mL, 10 ng/mL, 1 ng/mL, 100 pg/mL, 10 pg/mL and 1 pg/mL). The experiments for each concentration were conducted three times.

Biosensing of Cathepsin-G:

The current detection method is based on the measurement of Cathepsin-G proteolytic activity using a specific substrate peptide. The probe was designed to be specific to Cathepsin-G. Accordingly, the substrate sequence AAP- PFFK with Ahx (Aminohexanoic acid) linkers on either terminal of the peptide was used. The N-terminal of the peptide was attached to the magnetic bead. A cysteine residue was inserted at the C-terminal, permitting a gold-sulphur irreversible interaction for the establishment of a SAM layer of the peptide and magnetic bead on the surface of the sensor support (FIG. 1). Similarly, a round permanent paper magnet was fitted on the back and beneath the support (FIG. 1). Next, the Cathepsin-G enzyme was dropped over the functionalized sensor support. As described previously during proteolytic cleavage, the permanent magnet would attract the cleaved magnetic beads and cause a visual observation of the bright gold surface, offering qualitative evaluation of the examined samples. In addition, a quantitative evaluation was manageable by using different concentrations of Cathepsin-G solution, (100 ng/mL, 10 ng/mL, 1 ng/mL, 100 pg/mL, 10 pg/mL, 1 pg/mL and 100 fg/mL). All experiments were conducted three times.

Saliva Collection

Unstimulated human whole saliva was collected (a biological sample) under consistent conditions in the morning and during the day (from 7:00 in the morning to lunch time) with no eating and/or smoking 2 hours prior to collection. The saliva was collected from one individual. Saliva was then spiked with the HNE enzyme (using 50 µl of saliva and 20 µl of various HNE enzyme concentrations). A negative control using non-spiked saliva was tested to check whether the individual's saliva reacted with the already functionalized magnetic beads. The experiments were conducted three times.

Periodontal Patient Samples Testing

To study the clinical applicability of the developed biosensors, gingival creviculare fluid from patients suffering from periodontitis was utilized. The devices used were of various types. Syringes, saliva collectors, dentist tools, droppers to name a few. The study was approved by the Institutional Ethical Board of the Acedemic Hospital Vrije Universiteit at Amsterdam and informed consent was obtained from all donors. The patient samples were randomly selected for testing on HNE specific, Cathepsin-G specific and multiplexing supports. The patient samples were blotted on the support containing the SAM layer of HNE and Cathepsin-G beads. The experiments were conducted three times.

Multiplexing the Colorimetric Sensor Probe for Periodontal Inflammation Detection Two narrow pieces (1.5-2.0 mm in width) were cut and stacked over the plastic pH to provide a physical support for the bio-functionalization process of the detective sensor. The magnetic peptide solutions of each HNE and Cathepsin-G were mounted over each gold sensing surface and left at room temperature until dry. Consequently, an external magnetic field was applied using a permanent magnet with strength of 3360 gauss and 573 gauss at 1 mm and 10 mm distance, respectively. The magnet was passed over the functionalized strip from a distance of 3 mm to 5 mm to remove any non-immobilized magnetic beads. A round permanent paper magnet was fitted on the back and beneath the support. Next, several tests were conducted, where the HNE and Cathepsin-G enzymes were blotted over the functionalized sensor support. The experiments were conducted three times.

Progress in nanotechnology in the field of biosensors has improved and enhanced the application of biosensors. Generic colorimetric sensors which monitor biomarkers via degradation of thin films in the presence of an analyte is a promising approach for sensing biological processes in a disposable sensor format. The choice of the thin film material is based on the selection of a generic material that could be cleaved specifically by the biomarker of interest. A high degree of specificity could be achieved using films composed of a known natural substrate. However, colorimetric biosensors are capable of detecting protease activity providing accurate diagnostic and monitoring techniques for many diseases, such as Prostate cancer and inflammations such as periodontal diseases.

As reported in literature, HNE protease level and activity increases during periodontal disease resulting in the loss of the attachment between teeth and supporting tissues. Similarly, Cathepsin-G protease levels and activity are also elevated during periodontal inflammation resulting in the degradation of inflamed gingival connective tissues. Furthermore, Cathepsin-G is correlated with periodontal disease severity. Thus, these proteases could both serve as potential markers for the detection of periodontal diseases and disease progression.

In this study, the generic sensor concept was initially demonstrated using the periodontal markers HNE and Cathepsin-G and their peptide sequences AAPVAAK and AAPFFK. However, to ensure enzyme accessibility, the chosen specific HNE peptide sequence was linked to an additional 7-residue linker on either terminal; while the Cathepsin-G sequence was attached with Ahx linkers on either terminal of the peptide. These linkers were placed to enhance the access of the protease to the substrate sequence near the sensor surface and magnetic bead layer by providing additional degree of freedom to the target molecule. The N-terminal of the peptide was attached to the magnetic bead and a cysteine residue was added at the C-terminal, allowing a gold-sulphur interaction, and resulting in the formation of a SAM layer of peptides (HNE and Cathepsin-G) and magnetic bead on the gold sensor surface. Subsequently, the sensor chips were tested separately with purified proteases, saliva spiked with HNE and Cathepsin-G and periodontal patient samples.

Determine the Limit of Detection of HNE and Cathepsin-G

The constructed sensor was tested to detect the proteolytic activity of HNE and Cathepsin-G, by blotting 100 ng/mL of both enzyme solutions independently, over the functionalized gold sensor. The catalytic effect of both proteases induced the release of the peptide-magnetic bead moiety from the sensor surface, and the cleavage process was accelerated by the presence of the round paper magnet attached at the back of the sensor. The dissociation of the peptide-magnetic bead moiety from the gold sensor surface exposed the golden color of the sensor surface which was visible to the naked eye as seen in FIGS. 2A, 2B and 2C (for HNE) and FIGS. 5A, 5B and 5C (for Cathepsin-G).

In general, this biosensing method can be used for a quantitative detection of HNE as well as Cathepsin-G. After blotting different concentrations (1 pg/mL, 10 pg/mL, 100 pg/mL, 1 ng/mL, 10 ng/mL and 100 ng/mL) of the HNE enzyme and different concentrations (100 fg/mL, 1 pg/mL, 10 pg/mL, 100 pg/mL, 1 ng/mL, 10 ng/mL, and 100 ng/mL) of the Cathepsin-G enzyme independently onto the functionalized gold sensor. In the presence of the permanent magnet attached to the strip, we observed a steady increase in the visible bare gold surface in comparison with the enzyme solution concentration (FIGS. 2A, 2B and 2C, FIGS. 5A, 5B and 5C). This method proved to be sensitive and specific allowing the detection limit to be as low as 1 pg/mL for HNE and 100 fg/mL for Cathepsin-G. The non-specific protease (Blank) showed to have no reaction on the HNE and Cathepsin-G peptide-magnetic complex, since the sensor demonstrated no disruption of the SAM layer as shown in FIGS. 2A, 2B and 2C, FIGS. 5A, 5B and 5C. The detection limit is evidently better than the recently reported detection limits of hydrogel degradation films.

Determine the Limit of Detection of HNE and Cathepsin G in Spiked Saliva

The constructed sensor was validated using saliva sample provided by an individual with no history of periodontal diseases. The saliva was spiked with different concentration of HNE (1 pg/mL, 10 pg/mL, 100 pg/mL, 1 ng/mL, 10 ng/mL and 100 ng/mL) and different concentration of Cathepsin-G independently (100 fg/mL, 1 pg/mL, 10 pg/mL, 100 pg/mL, 1 ng/mL, 10 ng/mL, and 100 ng/mL). Each concentration of spiked saliva was blotted onto the functionalized gold sensor for five seconds or so, under the effect a permanent magnet attached to the strip. Clearly, a steady increase of the visible bare gold area in comparison with the HNE and Cathepsin-G enzyme solution concentration was perceived (FIGS. 3A, 3B and 3C, FIGS. 6A, 6B and 6C). The limits of detection for both spiked proteases were comparable to those obtained with the purified proteases. The non-spiked saliva was used as the negative control; the result proved no cleavage of the magnetic beads-peptide and no significant change in the sensor surface black color (FIGS. 3A, 3B and 3C, FIGS. 6A, 6B and 6C).

Detection of HNE and Cathepsin-G Proteolytic Activity in Periodontist Patients

Figure 4:
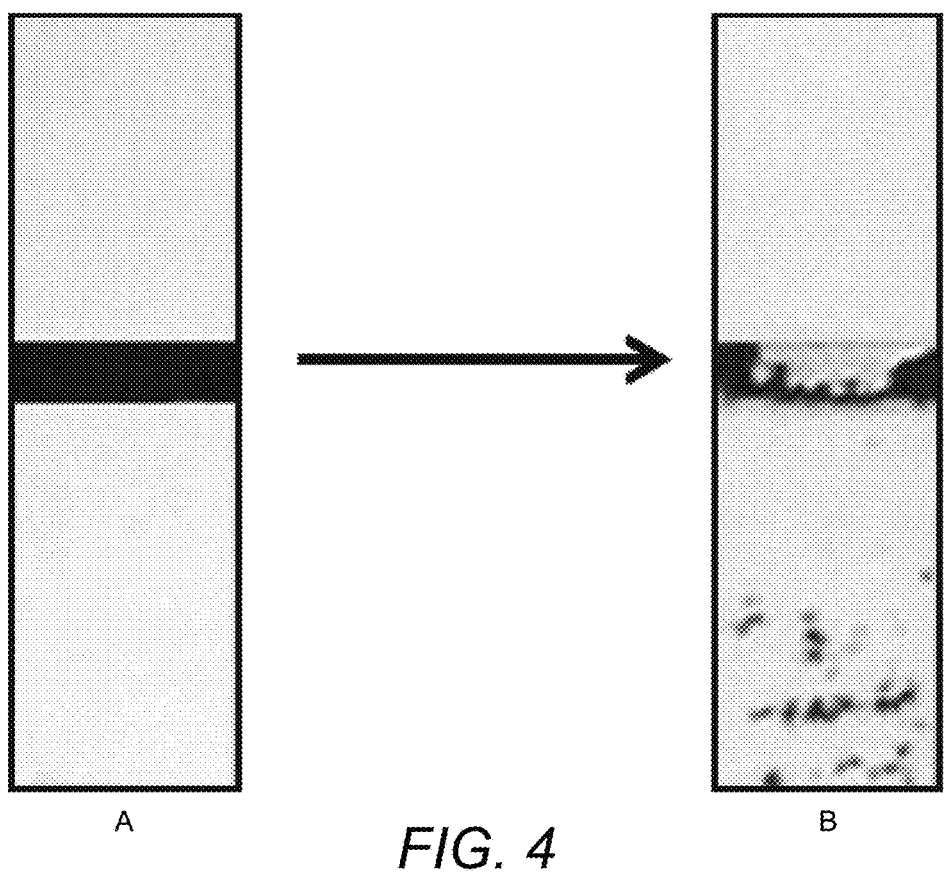
FIG. 4 shows example of a HNE marker application on patient sample in panel A of healthy control saliva (Negative result) and panel B of Periodontitis patients' saliva (Positive result).
Figure 7:
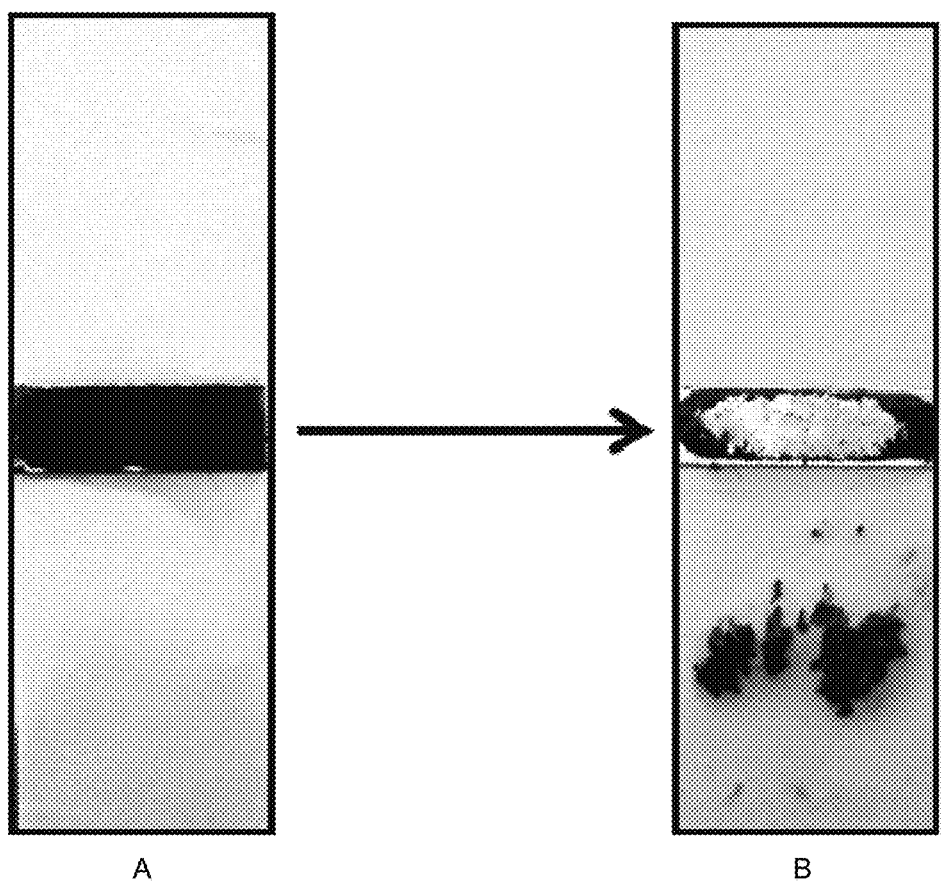
FIG. 7 shows Cathepsin-G marker application of patient sample. (A) Examination of healthy control saliva. (B) Examination of Periodontitis patients' saliva.
Figure 8:
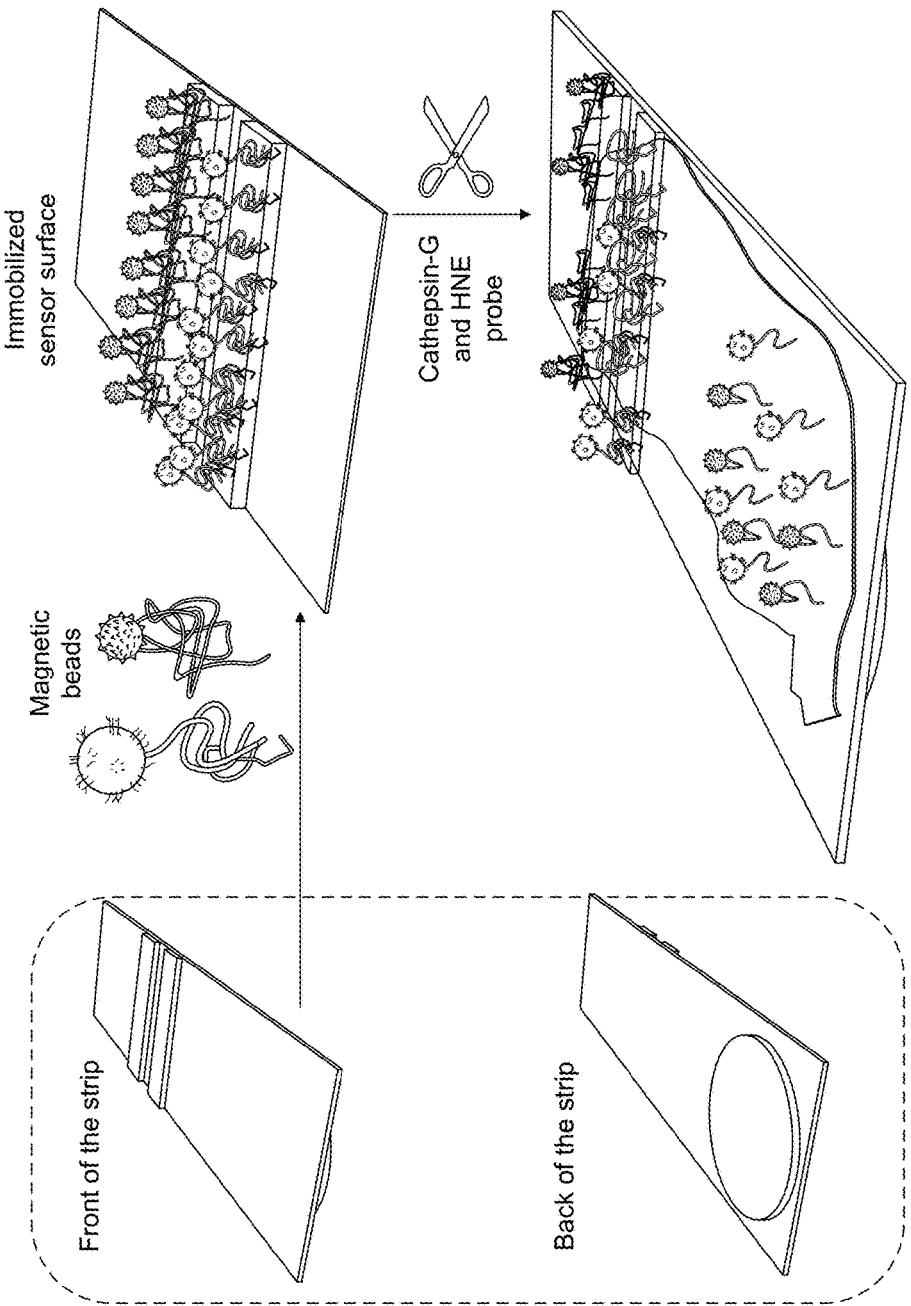
FIG. 8 is a schematic representation of simultaneous detection of HNE and Cathepsin-G in a gold support sensor.
Figure 9:
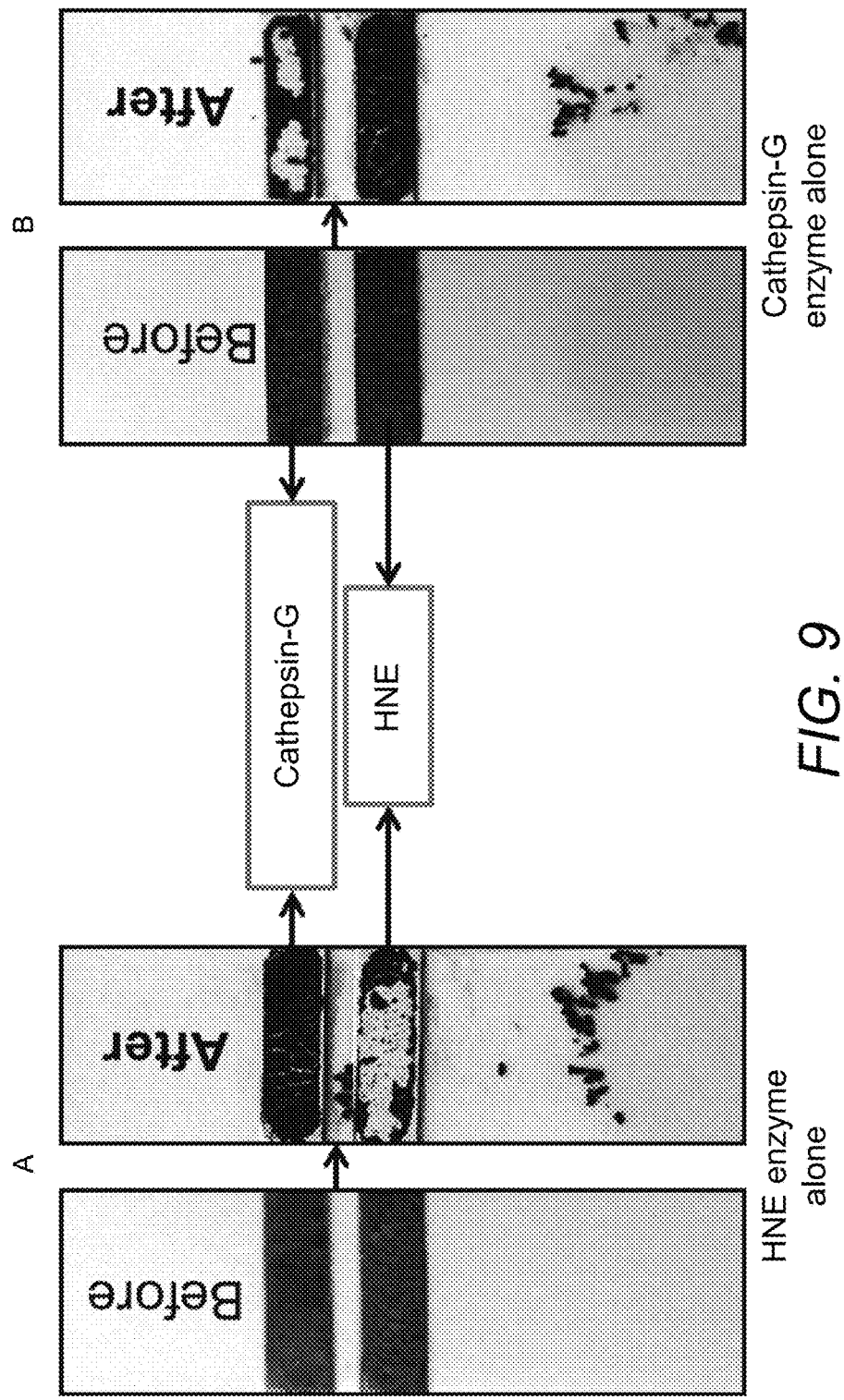
FIG. 9 shows individual peptide experimentation on gold support sensor.

Our sensor was also validated by testing several samples obtained from patients with periodontal disease. A full positive result was shown by the clear cleavage of the magnetic beads-peptide layer of HNE and Cathepsin-G and the consequent appearance of the sensor golden surface color (FIG. 4 and FIG. 7). The non-spiked saliva was used as the negative control for both proteases; the result proved no cleavage of the magnetic beads-peptide without any disruption of the SAM layer.

Multiplex Colorimetric Periodontal Inflammation Sensor Probe Under the Effect of Different Periodontal Enzyme Markers A further development of the marker was carried out where both markers were tested at once. Two pieces of the gold sensor surface were placed onto the pH strip and the magnetic-peptide complex of Cathepsin-G (Top band) and HNE (Bottom band) were mounted over the gold sensor surface and allowed to dry at room temperature ensuring proper gold sensor surface functionalization (FIGS. 8, 9, 10A, 10B, 10C, 10D and 10E and 11). At this stage, the golden color of the sensor chip was completely concealed. Afterward, an external magnetic field was passed over the functionalized gold sensor surfaces to remove any non-immobilized magnetic bead. The cleavage process was hastened by the existence of the round paper magnet which was placed at the back of the sensor. The sensor was then ready for Cathepsin-G and HNE detection.

The first set of experiments conducted on the multiplex colorimetric sensor probe was the examination of the activity of each individual protease on the functionalized sensor. The concentration of each protease was selected based on the highest activity seen in previous results (FIGS. 2A, 2B and 2C, FIGS. 5A, 5B and 5C). In both Cathepsin-G and HNE results (FIGS. 2A, 2B and 2C, FIGS. 5A, 5B and 5C), the highest concentration used was 100 ng/mL. The results obtained for both Cathepsin-G (FIGS. 5A, 5B and 5C) and HNE (FIGS. 2A, 2B and 2C) showed that the concentration selected had maximum cleavage.

In theory, there is no claim that HNE peptide sequence can be cleaved by the Cathepsin-G enzyme or vice versa. The reason for this is that these sequences are specific and sensitive to the specific protease, which has been proven in a previous study. Therefore, when the HNE enzyme alone was blotted onto the sensor strip, there was no cleavage seen on the top band containing Cathepsin-G and maximum reaction was seen in the bottom band containing HNE (FIG. 9A). Similarly, when the Cathepsin-G enzyme alone was blotted, there was no cleavage seen in the bottom band and there was maximum reaction seen in the top band (FIG. 9B). These results indicate that the peptide sequences for both proteases are specific and sensitive. Furthermore, no cross-reaction was observed.

The second set of experiments conducted was the examination of mixed enzymes (Cathepsin-G and HNE) at different ratios. The selected concentration of both enzymes was again 100 ng/mL. The various ratios of the mixed enzymes used were: 0 μL of Cathepsin-G to 100 μL of HNE (FIG. 10A), 25 μL of Cathepsin-G to 75 μL of HNE (FIG. 10B), 50 μL of Cathepsin-G to 50 μL of HNE (FIG. 10C), 75 μL of Cathepsin-G to 25 μL of HNE (FIG. 10D) and 100 μL of Cathepsin-G to 0 μL of HNE (FIG. 10E).

The examination of mixed enzymes at different ratios was conducted to determine the variance in the cleavage reaction for both markers. Therefore, the mixtures of enzymes with different ratios were blotted onto the sensor. The first result obtained showed there was no reaction seen on Cathepsin-G (Top band) and maximum cleavage was seen on the HNE sensor (Bottom band) where a golden color change was visible as seen in FIG. 10A. However, the results of the ratio of mixed enzyme (25 μL of Cathepsin-G to 75 μL of HNE) showed a minimum reaction on the Cathepsin-G (Bottom band) and a decline in the cleavage of the HNE sensor as the visible color change to gold is reduced compared to the 0:100 ratio of HNE (FIG. 10B).

On the other hand, the results of the mixture of enzymes under the 50:50 μL ratio (FIG. 10 C) demonstrated a visible equal reaction of both Cathepsin-G and HNE (top and bottom bands). There was an equal color change from black to gold after blotting the mixture of enzyme as shown in FIG. 10C. Moreover, the results of the mixture of enzymes under the 75 μL Cathepsin-G: 25 μL HNE ratio, showed an increase in the color change from black to gold of the Cathepsin-G sensor, while a decline in the cleavage of the HNE sensor was observed (FIG. 10D), indicating the reaction worked in a similar fashion to the ratio provided. However, the cleavage reaction of Cathepsin-G (75) was not equivalent to the HNE result (75).

The final results (FIG. 10E) obtained showed there was no reaction seen on the HNE sensor (Bottom band) and maximum cleavage was seen on the Cathepsin-G sensor (Top band) where a golden color change was visible to the naked eye. However the results obtained of Cathepsin-G (100) was not equivalent to the HNE cleavage (100), since there was more reaction seen in the HNE results (FIG. 10A) compared to the Cathepsin-G results (FIG. 10E). In general, these results observed showed similar activity and cleavage of the enzyme to the ratios provided.

Figure 11:
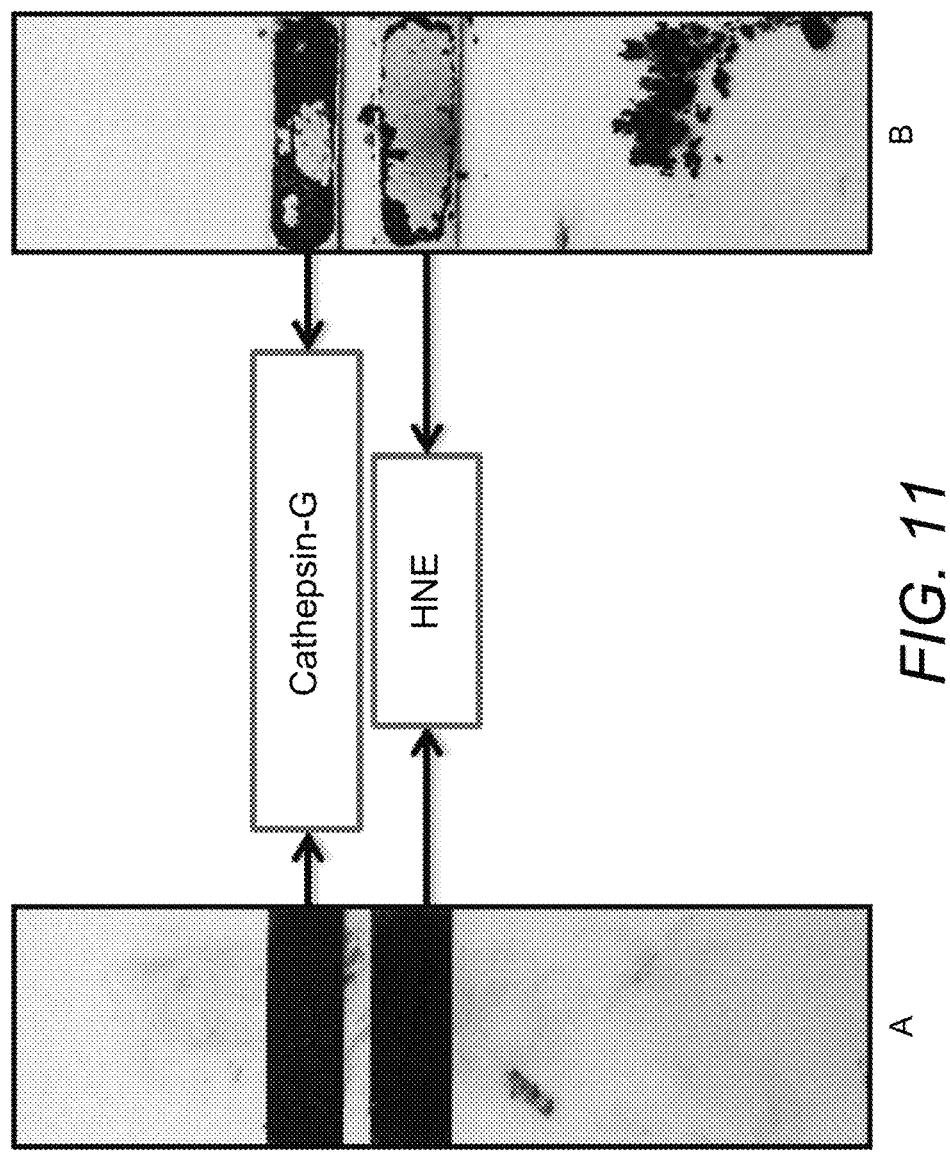
FIG. 11 shows simultaneous detection of two peptides in human saliva samples.

The final set of experiments conducted were the authentication of the multiplex sensor by testing several samples provided by patients with periodontal disease. A full positive result was observed and determined by the clear cleavage of the magnetic beads-peptide layer of Cathepsin-G (top band) and HNE (bottom band), since a consequent appearance of the sensor golden surface color was observed. However, the cleavage of the magnetic beads peptide layer of Cathepsin-G was seen to be lower than HNE but there was still a visible gold surface seen and the result was positive (FIG. 11). The results obtained showed a variation in the activity of the Cathepsin-G and HNE, this indicated that the sensor is specific and sensitive since the results were not the same for every patient sample. Normal individuals' saliva samples were also tested and no reaction was seen and the black color of the beads was maintained on the surface sensor (FIG. 11A).

The measurement of the detection, presence and intensity or absence of a disease, reading the progression, effect of treatment can also be observed not only calorimetric measurements but also using at least one of an electrochemical impedance (cyclic voltammetry) technique, electrochemical technique, optical (surface plasmon resonance (SPR), localized surface plasmon resonance (LSPR)), optical waveguide, mass sensitive sensors, surface enhanced Raman spectroscopy (SERS), colorimetric technique and a combination thereof.

Figure 12A:
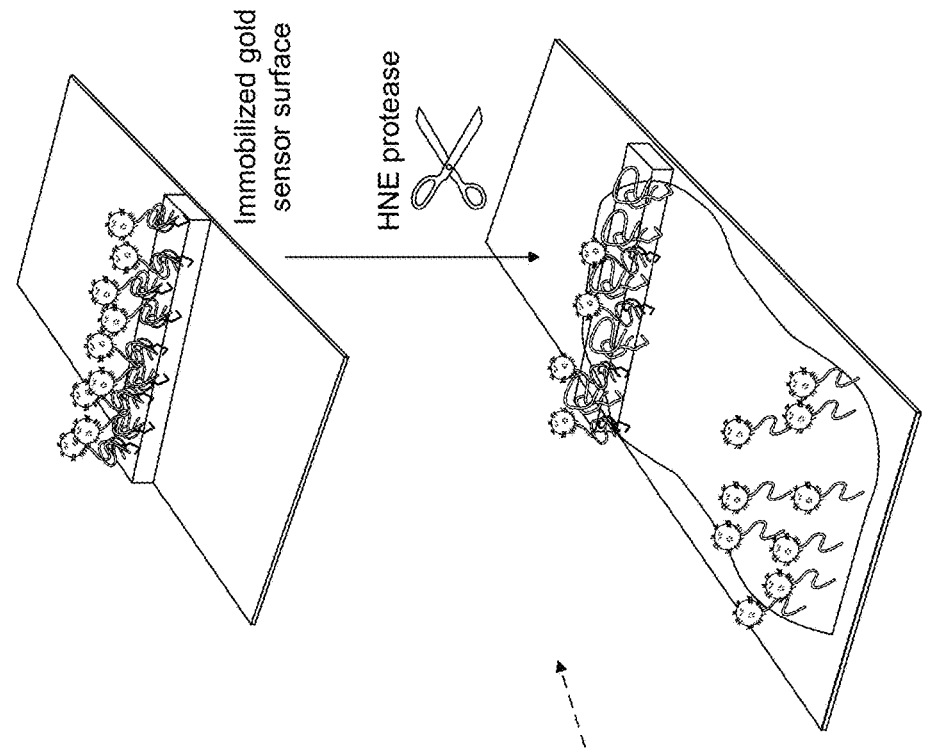
FIGS. 12A, 12B, 12C and 12D show integration of the devices into various support tools.
Figure 12A:
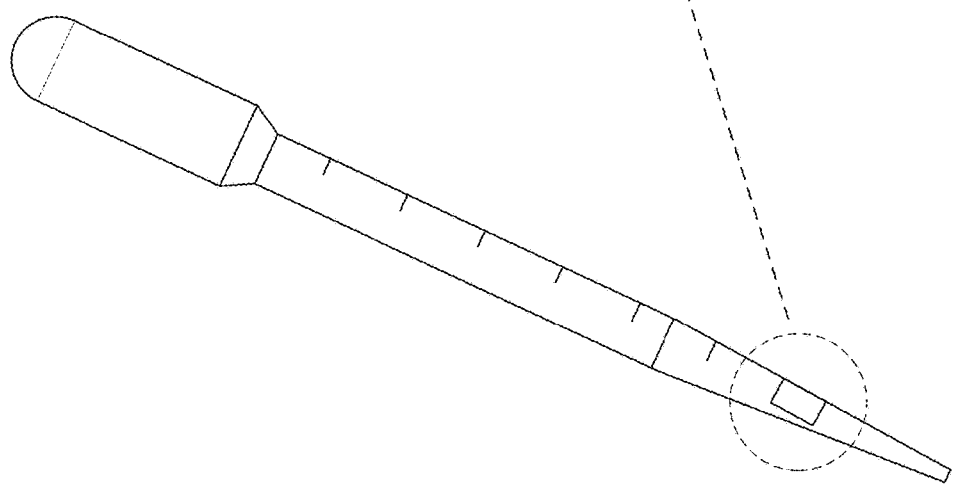
Figure 12B:
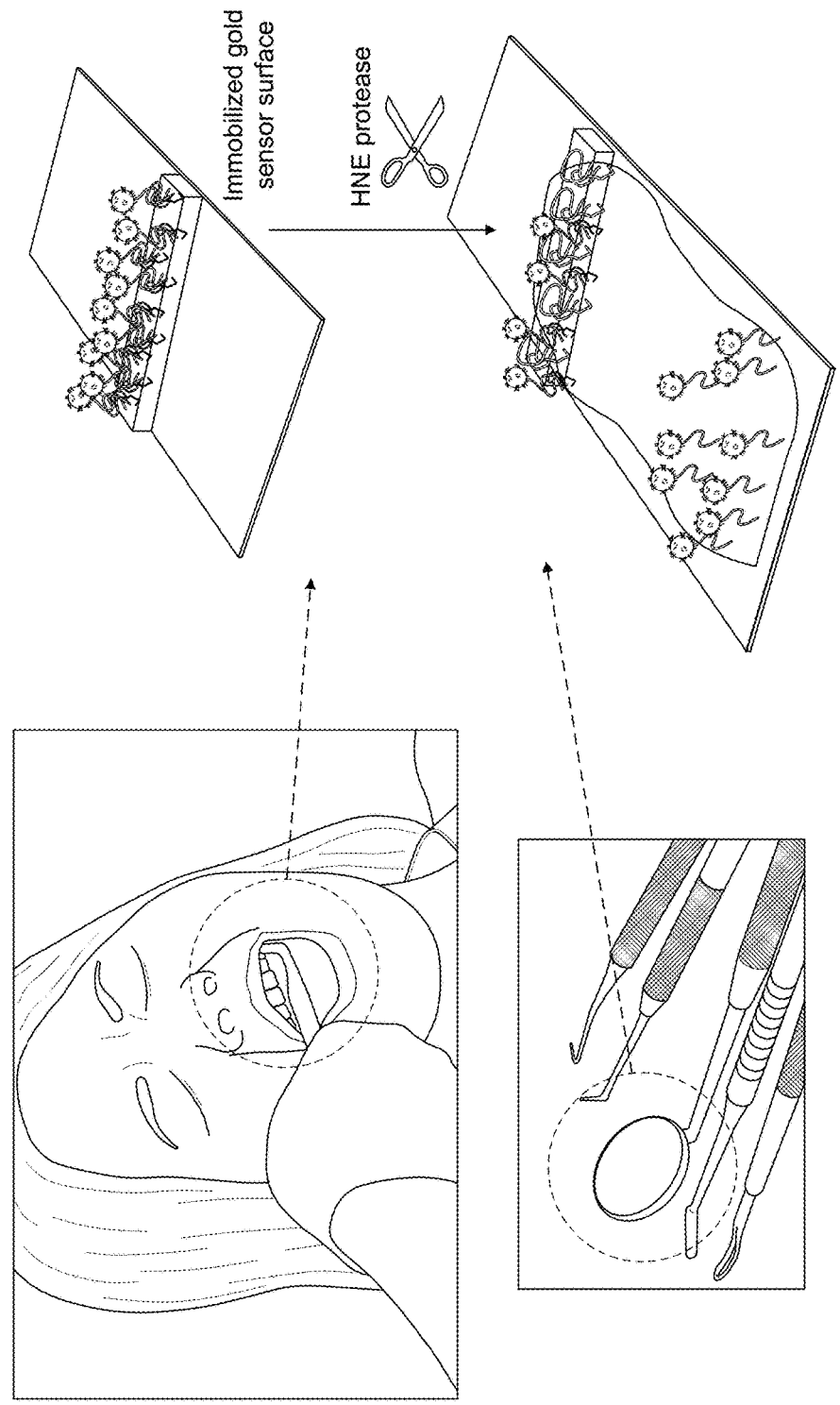
Figure 12C:
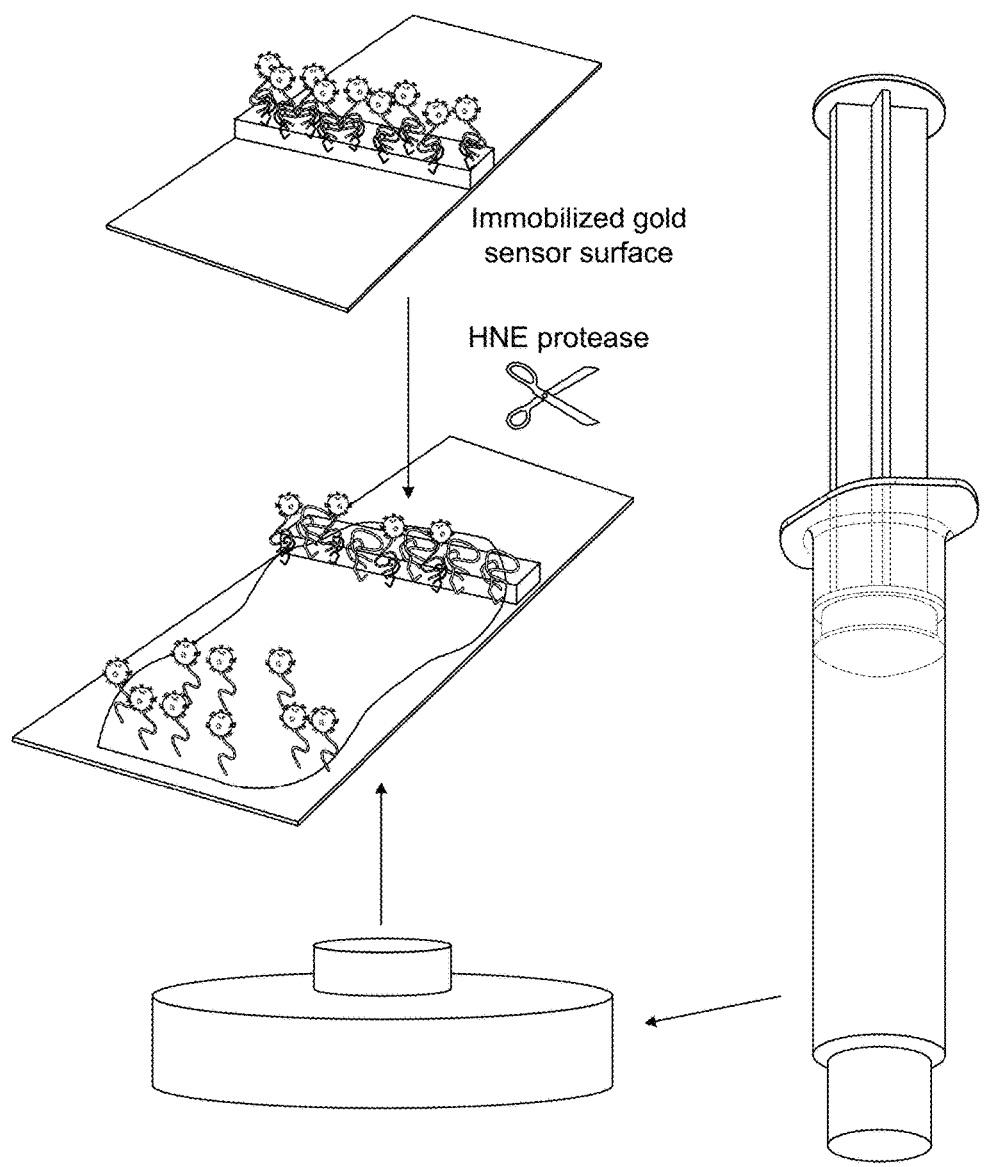
Figure 12D:
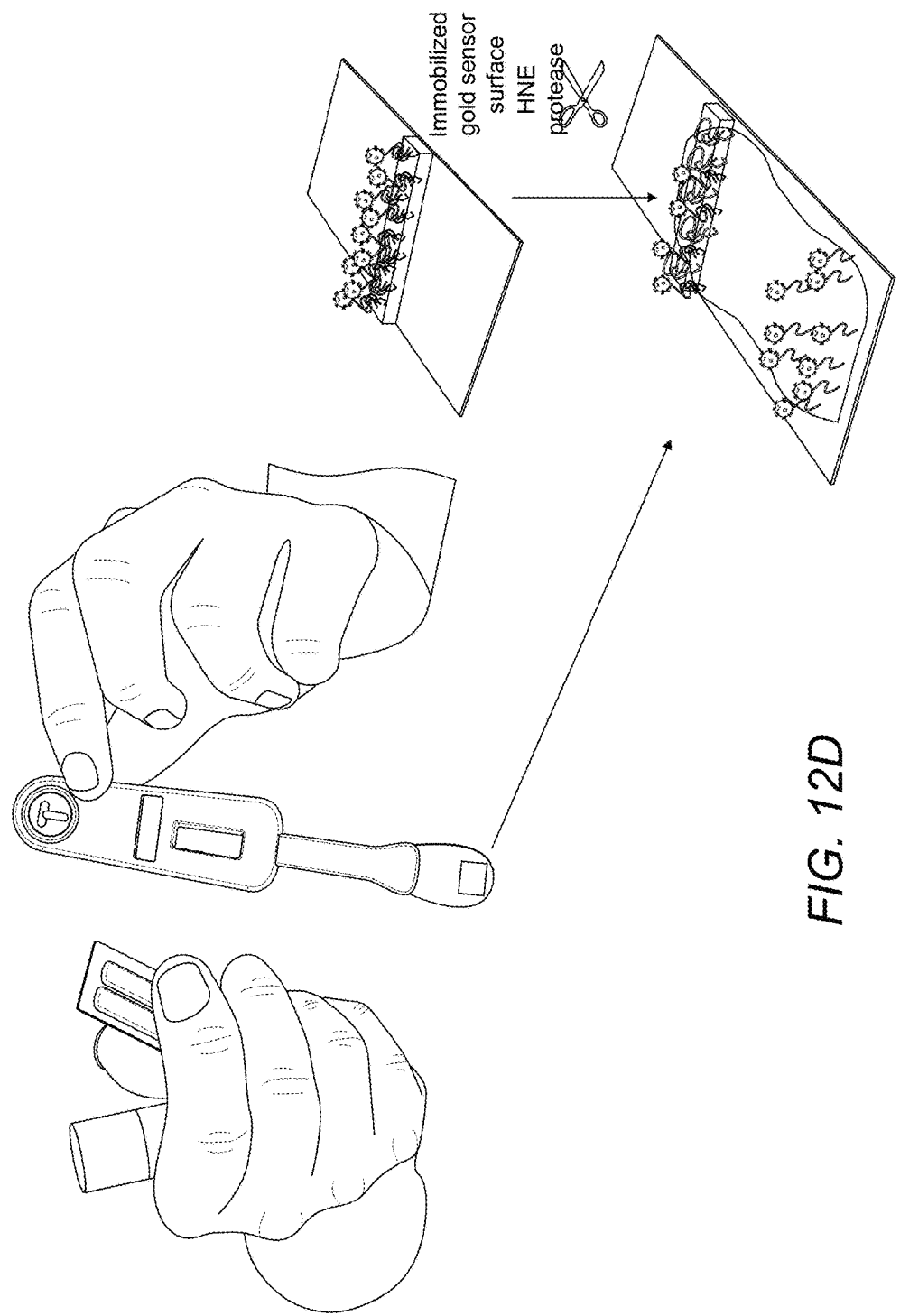

FIG. 12A shows that the dropper can be fitted with the magnetic nanoparticle biosensor. Another example is 12B that shows a dentist tool is fitted with the device. FIG. 12C shows that syringe has been fitted with device for use. FIG. 12D shows a saliva collector and the magnetic nanoparticle biosensor embedded or attached to the saliva collector to make a device.

INDUSTRIAL USE

The developed low-cost colorimetric sensor can be utilized with no prior technical knowledge and without the aid of any sophisticated instrumentation. Certainly, the approach is grounded on a one-step sensitive monolayer preparation using the SAM method. In addition, this assay is a wash-less process based on the analyte protease-induced detachment of the monolayer. The recognition device does not require any labelling or amplification schemes. Moreover, the protease recognition signal is an increase of the golden surface that is observable by the naked eye.

In addition, it will be appreciated that the various sequences, immunization processes, and methods of treatment disclosed herein may be embodied using means for achieving the various combinations of therapeutic dosage and delivery methods to treat a specific disease. Accordingly, the specification and drawings are to be regarded in an illustrative rather than a restrictive sense.

---

What is claimed is:

1. A method to detect two periodontal marker enzymes in combination to diagnose a periodontal disease, comprising:
   conjugating of a Human Neutrophil Elastase (HNE) and a Cathepsin-G substrate peptide and their substrate sequences Seq ID No. 3 and Seq ID No. 4 to magnetic beads to make a magnetic nanoparticle biosensor;
   preparing more than one self-assembled monolayer of peptide coupled carboxy terminated magnetic bead on a gold sheet to form a gold sensor support, wherein a top monolayer comprises a Cathepsin-G peptide complex and a bottom monolayer comprises a HNE peptide complex;
   fitting a round permanent magnet on back of the gold sensor support;
   reacting the gold sensor support by applying the biological sample which contains a protease to cleave the Cathepsin-G enzyme and HNE enzyme in a specific concentration; and
   measuring the association or dissociation of the peptide coupled carboxy terminated magnetic bead on the gold sensor support to detect presence and intensity or absence of the periodontal disease in a human.

2. The method of claim 1, wherein the specific concentration of the Cathepsin-G enzyme and Human Neutrophil Elastase enzyme present in the saliva is between 1 pg-100 ng.

3. The method of claim 1, wherein the biological sample is a saliva.

4. The method of claim 1, wherein the measuring is done using at least one of an electrochemical impedance (cyclic voltammetry) technique, electrochemical technique, optical (surface plasmon resonance (SPR), localized surface plasmon resonance (LSPR)), optical waveguide, mass sensitive sensors, surface enhanced Raman spectroscopy (SERS), colorimetric technique and a combination thereof.

5. The method of claim 1, wherein the gold sensor support is located in a support tool, wherein the support tool is at least one of a dentist tools, syringe, swab, a dropper, paper sensor support, cotton, piece of cotton, piece of cloths, or any other metal sensor support which is dielectric or an insulator, any other small instrument that may come in contact with a biological fluid and enable it to flow or collect and deliver it to the magnetic nanoparticle biosensor device.

* * * * *